(12) United States Patent
Kholodkevich et al.

(10) Patent No.: US 8,442,809 B2
(45) Date of Patent: May 14, 2013

(54) METHOD FOR BIOLOGICALLY MONITORING THE ENVIRONMENT (VARIANTS) AND A SYSTEM FOR CARRYING OUT SAID METHOD

(76) Inventors: Sergei Viktorovich Kholodkevich, St.Petersburg (RU); Alekesi Valentinovich Ivanov, St.Petersburg (RU); Evgeny-Leonidovich Kornienko, St.Petersburg (RU); Anton Sergeevich Kurakin, St.Petersburg (RU)

( * ) Notice: Subject to any disclaimer, the term of this patent is extended or adjusted under 35 U.S.C. 154(b) by 517 days.

(21) Appl. No.: 12/308,040

(22) PCT Filed: Jun. 15, 2007

(86) PCT No.: PCT/RU2007/000338
§ 371 (c)(1),
(2), (4) Date: Oct. 14, 2010

(87) PCT Pub. No.: WO2008/048141
PCT Pub. Date: Apr. 24, 2008

(65) Prior Publication Data
US 2011/0028849 A1    Feb. 3, 2011

(30) Foreign Application Priority Data

Jun. 20, 2006  (RU) .............................. 2006122457

(51) Int. Cl.
*G06G 7/48*    (2006.01)
*G06G 7/58*    (2006.01)
*G01N 33/48*   (2006.01)
*G01N 31/00*   (2006.01)

(52) U.S. Cl.
USPC .................... 703/11; 703/12; 702/19; 702/22

(58) Field of Classification Search .................. None
See application file for complete search history.

(56) References Cited

U.S. PATENT DOCUMENTS 5,239,180 A * 8/1993 Clarke ..................... 250/339.11

OTHER PUBLICATIONS

Kamenos et al. (Animal Behaviour, 2006, 71(4), 809-813).*
Depledge et al. (Comp. Biochem. Physiol., 1990, 96A(4), 473-477).*

* cited by examiner

Primary Examiner — Larry D Riggs, II
(74) Attorney, Agent, or Firm — Vera Chernobylsky

(57) ABSTRACT

The invention relates to ecological environment monitoring based on native animals functional state control. The method includes exposure a test animal to IR radiation using an optical radiation source and a transmitting optical fiber; receiving the reflected IR radiation using a receiving optical fiber; converting the reflected IR radiation to an electrical signal; determining a sample of values of the signal periods and the sample dispersion; and forming a danger signal when the threshold value exceeds the sample dispersion. The system contains a cardiac activity sensor which includes a transmitting and receiving optical fibers, an optical radiation source and optical radiation receiver; an amplifier, an analog-to-digital converter and a computer. The output end of transmitting fiber and the input end of receiving fiber have the same direction and are positioned at a distance R satisfying the inequality $(\pi d^2 P)^{0.07} - 2.2(1/(\pi d^2 P))^{0.02} \leq R \leq (\pi d^2 P)^{0.07} + 2.2(1/(\pi d^2 P))^{0.02}$.

17 Claims, 3 Drawing Sheets

METHOD FOR BIOLOGICALLY MONITORING THE ENVIRONMENT (VARIANTS) AND A SYSTEM FOR CARRYING OUT SAID METHOD

PERTINENT ART

The invention relates to the field of environment conservation, in particular, methods and means of ecological environment monitoring with the help of a non-invasive control of functional state of native animals. The invention can be predominantly used for automatic on-line estimation of the quality of environment components such as water, bottom sediments, air and soil on the basis of remote real-time registration of physiological activity parameters, first and foremost, cardiac activity in invertebrates with a hard outer covering, e.g. crayfish, crabs, shell mollusks, insects or arachnids.

PRIOR ART

For remote automatic real-time biological monitoring of the environment basing on control of physiological activity of test organisms it is possible to use various animal species whose selection is determined by their habitat and presence on their body of a hard outer covering that makes it possible to set up an animal's physiological activity sensor thereon. Thus, for example, vine snails, achatines, scorpions and mole crickets can be used to estimate the quality of air and soil, whereas crabs, crayfish, spiny lobsters, lobsters and shell mollusks living in water to estimate the quality of water and bottom sediments. Means of biological monitoring are nowadays most widely used to estimate the quality of aquatic environment. As shown by an analysis into the state of the art technology in this field, animals such as fish, crabs, crayfish, spiny lobsters, lobsters and shell mollusks, e.g. oysters, mussels, various species of unionides and gastropod mollusks can be used for the purposes of automatic on-line real-time estimation of the quality of aquatic environment basing on remote control of hydrobionts' physiological activity.

A method of real-time biological monitoring of physiochemical parameters of aquatic environment is known (EP0730736, 1996, WO95/14925, 1995), which includes placing tropical fish of *Apteronotus albifrons* variety that are physiologically able to emit electrical signals with a frequency of about 1000 Hz and are used as test animals in perforated capsules installed in a tank for running water under investigation and maintenance, with the help of a thermoregulation system, of a preset temperature of water under investigation with an error not exceeding $0.1°$ C. The method also provides for receiving electrical signals emitted by fish with the help of metal electrodes positioned in water under investigation inside the tank; amplifying these electrical signals; converting them to digital codes; entering digital codes into a computer; processing the digital codes by a computer in order to determine parameters of electrical signals received; and decision-making about ecological danger in case parameters of electrical signals received deviate from the preset values.

Disadvantages of this known method are insufficiently high reliability of aquatic environment monitoring, which is connected with a significant dependence of parameters of electrical signals emitted by fish on the temperature of water under investigation rather than on its ecological danger; high complexity and cost of equipment realizing it, which complexity and cost is connected with the necessity to use a high-precision thermoregulation system; as well as a fairly high operating cost of said equipment, which is conditioned, first, by its complexity and, second, by use of rare tropical fish species rather than native hydrobionts as test organisms. The scope of application of this known method is limited by the possibility of using it only to monitor water running through the aforementioned tank and does not extend to ecological monitoring of open water areas.

A method of estimating water quality is known (U.S. Pat. No. 6,393,899, 2002), which is based on registration and real-time analysis of respiratory activity signals from native freshwater fish, primarily, trout or perch since these species have sizeable gill covers. This known method provides for placing fish in exposure chambers with water under investigation and with two electrodes secured on each chamber in water under investigation above and below and made, e.g. from stainless steel or graphite; receiving and converting, with the help of said electrodes, physiological signals arising during movement of test fish's gill covers to electrical signals of respiratory activity; transmitting these electrical signals via a wire communication line; amplifying and converting them to digital codes; entering digital codes obtained into a computer; processing the digital codes by the computer in order to determine respiratory rate and depth in test fish; and decision-making about ecological danger when respiratory rate and depth in test fish deviate from the preset values; and forming an alarm signal and further sampling water under investigation for chemical analysis.

This known method enables to form and register respiratory activity signals of fish that are native hydrobionts and also automatically make a decision about deterioration of the quality of aquatic environment under investigation basing on the change in fish's respiratory activity parameters that is conditioned by the stress developing in their organism and connected with deterioration of water quality.

However, using electrodes not electrically insulated against water as a sensor of the fish's physiological activity signal in this known method of water quality estimation, likewise in the above similar-purpose method, leads to instability of the signal formed by the electrodes and accompanied by a fairly intensive noise. First of all, this can be observed in the case of a significant electric conductivity of aquatic environment. Where stainless-steel electrodes are used, these two types of distortion of electrical signal being formed grow even higher due to galvanic interaction of stainless steel with water. Such distortions greatly complicate subsequent processing of the electrical signal formed and can lead to making a wrong decision about the state of aquatic environment under investigation.

As the authors of this known method note in the invention description, it is for the same reason that a change in electric conductivity of water under investigation greatly influences the electrical signal amplitude of fish's respiratory activity being formed. In particular, the growing electric conductivity of water leads to considerably lower amplitude of the fish's respiratory activity signal, which, first, can lead to missing it during registration. Second, a change in the fish's respiratory activity signal amplitude connected with a change in electric conductivity of water leads to wrong results in decision making absolutely not connected with actual changes in the quality of water under investigation. To make it feasible in practice, this known method of water quality evaluation provides for using, while processing the fish's respiratory activity signal, a partial algorithmic compensation for the change of its amplitude cause by the change in electric conductivity of water. This, however, led to a more complicated structure design and higher cost of the water quality evaluation system realizing this method, as well as made its use more complex owing to bringing about the necessity to regularly calibrate it using water of different electric conductivities.

Moreover, using a rather long wire line for connecting electrodes with the amplifier of the fish's respiratory activity signal in this known water quality evaluation method, as in the above similar-purpose method, for transmitting the formed fish's physiological activity signal causes additional distortion of the formed electric signal of fish's respiratory activity in consequence of inevitable external interference inductions, which can also lead to a wrong decision-making about the state of aquatic environment under investigation.

A method for biological monitoring of aquatic environment is known which is realized in the equipment for detecting aquatic environment pollution (FR2713738, 1995) and provides for using water bivalve shell mollusks, e.g. mussels. This known method includes gluing the lower valve of the mollusk's shell in water under investigation on a horizontally positioned base so that the upper valve of the mollusk's shell rests against an elastic plate secured to the base parallel with its surface and equipped with a magnet or metal plate at its end. The method also provides for forming a signal of motion activity of the mollusk's shell valves with the help of a Hall probe or inductive sensor installed on the base and interacting, respectively, with the magnet or metal plate; determining the frequency of a signal of motion activity of mollusk's shell valves; and decision-making about ecological danger when the frequency of this signal exceeds the preset value.

This known method of biological monitoring of aquatic environment enables to form and register motion activity signals of mollusk's shell valves, as well as automatically make a decision on deterioration of the quality of aquatic environment under investigation, which is conditioned by the stress developing in the mollusk organism and connected with deterioration of water quality.

At the same time, the method provides for securing the test mollusk by gluing the lower valve of its shell to the horizontal base in the position, which differs from the mollusk's position under its natural life conditions by a split between the shell valves oriented upwards; as well as placing it between the base and elastic plate which owing to mechanical contact and its elastic properties exerts a considerable pressure upon the upper shell valve, thus preventing it from opening. This may, first, cause in this animal the state of stress that is by no means connected with a change in the quality of aquatic environment under investigation, but may lead to a wrong decision-making about the quality of water under investigation. Second, the same reason can cause a disease or even death of the test animal, which leads to complication and higher operating cost of the equipment realizing this method in connection with the necessity to more frequently replace test animals in consequence of their disease or death.

In addition, using in this known method a wire communication line for transmitting an electrical signal from the Hall probe or inductive sensor does not protect this communication line against inevitable external interference inductions that distort the electrical signal of motion activity of the mollusk shell valves and can, therefore, lead to a wrong decision-making about the quality of aquatic environment under investigation.

Closest by its technical essence to the method of biological environment monitoring being the subject of this invention should be considered the computer-aided physiological monitoring method as implemented in a computer-aided physiological monitoring system CAPMON (Depledge M. H., Andersen B. B. A computer-aided physiological monitoring system for continuous, long-term recording of cardiac activity in sample invertebrates.—Comp. Biochem. Physiol., Vol. 96A, 1990, No. 4, p.p. 473-477). This known method can be used for monitoring aquatic environment and is based on non-invasive formation, registration and analysis of cardiac activity signals from crabs performing the function of test invertebrates. This computer-aided physiological monitoring method chosen as the closest prototype provides for installing on the test crab's carapace within its heart area a cardiac activity sensor including a hermetic casing, a light-emitting diode placed inside the casing as an optical radiation source and made so that it can emit optical radiation of near IR spectral range, and a phototransistor placed inside the casing as an optical radiation receiver sensitive to optical radiation of near IR spectral range; and placing the test crab in aquatic environment under investigation. The method also includes exposing the test crab's heart area to optical radiation of near IR spectral range emitted by the optical radiation source; receiving and converting the optical radiation reflected by the test crab's heart to an electrical signal with help of the optical radiation receiver; transmitting the received electrical signal via the wire communication line; amplifying the electrical signal; converting its instantaneous values to digital codes; entering the digital codes obtained to a computer; determining with the help of the computer and memorizing a sample of period values of the electrical signal received during the preset time interval; determining with the help of the computer a sample mean value of the period of the electrical signal received during the preset time interval; comparing with the help of the computer the obtained sample mean value of the electrical signal period with the threshold value set for it; and forming an ecological danger signal in case the threshold value exceeds the sample mean value of the period of the electrical signal received during the preset time interval.

This known method of computer-aided physiological monitoring enables to form and register cardiac activity signals from test crabs, as well as automatically make a decision about deterioration of the quality of aquatic environment under investigation basing on a change of such crabs' cardiac activity parameter as heartbeat period which is conditioned by the stress developing in their organism in connection with deterioration of water quality.

When exercising this known computer-aided physiological activity monitoring method chosen as the closest prototype, the use of a cardiac activity sensor designed to form an electrical signal and containing an optical radiation source and an optical radiation receiver installed in a hermetic casing sealed off the aquatic environment under investigation prevents the rise of instability of the electrical signal and noise accompanying it, including in the case of a significant electric conductivity of aquatic environment under investigation. This simplifies subsequent processing of the electrical signal formed and lowers probability of wrong decision-making about the state of aquatic environment under investigation.

For the same reason a change in electric conductivity of water under investigation exerts no influence on the amplitude of the electrical signal formed by the cardiac activity sensor, which makes for reliable registration of the electrical signal and lowers probability of wrong decision-making about the quality of water under investigation. Moreover, in processing the electrical signal this does not bring about the necessity to use algorithm compensation for the change of its amplitude caused by the change of water electric conductivity.

At the same time, the hermetic casing, with the optical radiation source and optical radiation receiver installed inside it, used in the structure of the cardiac activity sensor has a noticeable mass and dimensions. This is why placing such a casing, with the optical radiation source and optical radiation receiver installed inside it, on the crab's carapace can, first, cause in this animal the state of stress connected not with a change in the quality of aquatic environment under investigation, but rather with the presence of a rather massive and sizeable foreign body on the carapace. As a result, while processing the electrical signal formed by the sensor, a wrong decision could be made about the quality of water under investigation. Second, the same reason can induce a disease and even death of the test animal, which increases the cost and complicates operation of the computer-aided physiological monitoring system in connection with the necessity to more frequently replace test animals owing to their disease or death.

In addition, using, while implementing the method, a rather long wire line of communication between the optical radiation receiver of cardiac activity and the amplifier does not protect this communication line against inevitable external interference inductions that distort the electrical signal of crabs' cardiac activity not yet undergone power amplification, and in its further processing can lead to a wrong decision-making about the quality of aquatic environment under investigation.

Moreover, as shown in FIG. 4 of the article (Depledge M. H., Andersen B. B. A computer-aided physiological monitoring system for continuous, long-term recording of cardiac activity in sample invertebrates.—Comp. Biochem. Physiol., Vol. 96A, 1990, No. 4, p.p. 473-477) analyzing the method chosen as the closest prototype, an electrical signal formed by the cardiac activity sensor is, first, accompanied by an significant constant component and, second, has a rather complicated a priori unknown form unstable in time due to movements of the test animal. These circumstances lead to serious errors in determining the electrical signal period and, consequently, heartbeat period in the test animal, which, when further processed, can lead to a wrong decision-making about the quality of environment under investigation.

Finally, using in the computer-aided physiological activity monitoring method chosen as the closest prototype for making a decision on the state of environment under investigation a comparison with the set threshold value of the sample mean value of the period of the of the electrical signal received for the preset time interval, which value is proportional to the sample mean heartbeat period value, ensures no high-degree reliability of monitoring, narrows functional potentials of the method and also leads to higher cost and complication of operating the computer-aided physiological monitoring system realizing this known method, which is confirmed by the following considerations.

It is known that the transition of some invertebrate species with a hard outer covering, e.g. crustaceans and crabs from quiet state to the state of stress due to, for example, deterioration of environment quality is actually most often accompanied by a considerable reduction of the heartbeat period. Thus, for example, during transition from quiet state to stress state the heartbeat period in crayfish *Astacus astacus* L. and crabs *Carcinus maenas* likewise decreases by the factor of 2-3. As a result, there decreases the sample mean value of the heartbeat period and, consequently, that of the electrical signal period.

At the same time, experimental research conducted by the authors of this invention in laboratory and full-scale conditions to study cardiac activity in invertebrates with a hard outer covering showed that in some individual crayfish and crabs the transition to the state of stress is not for some reasons accompanied by perceptible reduction of the heartbeat period. The reasons for this are not established yet. The authors of the invention only presuppose that this is connected with peculiarities in the unfolding of nervous processes in different individuals of these animals similarly to that as this happens in people with different temperament types, as well as with peculiarities of the preceding development of each particular individual animal.

On the one hand, using as test organisms such individual animals, which while being under stress because of chemical pollution of environment only slightly decrease the duration of their heartbeat period, lessens environment-monitoring reliability. On the other hand, this brings about the necessity to preliminarily select animals for use as test organisms, which leads to higher cost and complication of using the computer-aided physiological monitoring system realizing the method chosen as its closest prototype. Here, if the aforementioned preliminary selection of animals is of a subjective nature, this also lowers environment-monitoring reliability. And the use in order to impart preliminary selection objectivity of conducting test experiments with sample animals in conditions of artificial pollution can cause a disease or death of animals, which makes the cost even higher and complicates the operation of the computer-aided physiological monitoring system. Furthermore, if the organism of experimentally sample animals adapts to artificial pollution, the use thereof as test organisms in ecological environment monitoring also leads to lower reliability of its control.

Moreover, said experimental research by the authors of the invention aimed to study cardiac activity of invertebrates with a hard outer covering also showed that in some species of these animals, for example, the huge majority of both shell mollusks living in water and shell mollusks living on land, e.g. achatines and vine snails, the heartbeat period can undergo no substantial changes during transition thereof to stress state, which is probably connected with peculiarities of their cardiovascular system. This limits the scope of application of the known method to only monitoring the state of aquatic environment and bottom sediments and does not allow using it to monitor the state of air and soil.

That is why disadvantages of the known computer-aided physiological monitoring method chosen as the closest prototype are insufficiently high reliability of environment monitoring, insufficiently wide functional potentials, as well as high cost and operation complexity of the system realizing it.

Among biological environment monitoring systems an equipment for real-time biological monitoring of physiochemical parameters of aquatic environment is known (EP0730736, 1996, WO95/14925, 1995), for which tropical fish of *Apteronotus albifrons* variety having physiological ability to emit electrical signals with the frequency of about 1000 Hz are used as test animals. This known equipment contains a reservoir for running water under investigation; a system for thermoregulation of the preset temperature of water under investigation with an error not exceeding 0.1° C.; at least one perforated capsule installed in the reservoir for placing test fish; metal electrodes installed in water under investigation inside the reservoir; an amplifier with an analog-to-digital converter connected to the electrodes and a computer with a monitor connected to the analog-to-digital converter output.

Disadvantages of this equipment for real-time biological monitoring of physiochemical parameters of aquatic environment are insufficiently, high reliability of aquatic environment monitoring, which is connected with a significant dependence of parameters of electrical signals emitted by fish on the temperature of water under investigation rather than on the scale of its ecological danger; as well as high complexity and cost of this equipment connected with the necessity to use a high-precision thermoregulation system. In addition, a disadvantage of this equipment is a rather high operating cost conditioned, first, by its complexity and, second, use of not native hydrobionts, but rare tropical fish species as test organisms. Also, the sphere of application of this equipment is limited by the possibility to use it only for monitoring water running through said reservoir and does not extend to carrying out ecological monitoring of open water areas.

A system for automatic biological water quality monitoring is known (U.S. Pat. No. 6,393,899, 2002) which is based on registration and analysis of respiratory activity signals from native freshwater fish, primarily, trout or perch species, since these have sizeable gill covers. This known system contains exposure chambers with water under investigation to place fish in it; two electrodes mounted on each chamber above and below in water under investigation, each of them being made from, e.g. stainless steel or graphite in order to ensure corrosion resistance and equipped with an electrode holder and hermetic connector assembly. In addition, beyond water under investigation the above system contains series-connected devices: an amplifier connected to the electrodes via a wire communication line; an analog-to-digital converter; controller; terminal panel and oscillograph; sampler and warning device connected to the terminal panel; as well as a remote computer, remote monitor and water-quality analyzer with a controlled electromagnetic valve, all connected to the controller.

This known system enables to form and register respiratory activity signals from fish being native hydrobionts, and also automatically make a decision on deterioration of the quality of aquatic environment under investigation basing on a change in fish's respiratory activity parameters conditioned by the stress developing in their organism and connected with deterioration of water quality.

However, using electrodes not electrically insulated against water as a sensor of fish's respiratory activity signal in this known system for automatic biological water-quality monitoring leads to instability of a signal formed by the electrodes and a rather intensive accompanying noise. First of all, this can be observed where aquatic environment has a significant electric conductivity. If electrodes are made from stainless steel, these two types of distortion grow even higher owing to galvanic interaction between stainless steel of electrodes and water. Such distortions greatly complicate further processing of the formed electrical signal and can lead to a wrong decision-making about the state of aquatic environment under investigation.

As the authors of this system note in the invention description, it is for the same reason that a change in electric conductivity of water under investigation greatly influences the electrical fish's respiratory activity signal being formed. In particular, an increase of electric conductivity of water leads to a considerable decrease of the amplitude of the fish's respiratory activity signal, which can, first, lead to overlooking it during registration. Second, a change in the amplitude of the fish's respiratory activity signal connected with a change of water electric conductivity leads during decision-making to erroneous results absolutely not connected with the change of the quality of aquatic environment under investigation. To improve performance of this system for automatic biological monitoring of water quality during the processing of the fish's respiratory activity signal, it provides for using partial algorithmic compensation for the change in its amplitude caused by a change of water electric conductivity. However, this led to sophistication of the structure and cost of this system and also complicated its operation, since this necessitated its periodic calibration using the water of different electric conductivity.

Moreover, using in the above known system for biological water-quality monitoring a rather long wire line of communication of electrodes with the amplifier causes additional distortions of the formed electrical fish's respiratory activity signal due to inevitable external interference inductions.

Equipment for detecting aquatic environment pollution (FR2713738, 1995) is known, which provides for using water bivalve shell mollusks, e.g. mussels, as test animals. This known equipment contains at least one sensor of motion of mollusk valves, which includes a horizontally positioned base, elastic plate secured to the base in parallel with its surface and equipped with a magnet or metal plate at its end, and the Hall probe or inductive sensor installed on the base so that they can interact with, respectively, the magnet or metal plate. The sensor of mollusk valves' motion in this case is made so that the mollusk can be glued with its lower shell valve on the base so that its upper shell valve comes up against the elastic plate. Besides, the aforementioned known equipment contains an amplifier, analog-to-digital converter, data processing unit based on a micro-controller, data collection unit, and warning unit.

This known equipment for detecting aquatic environment pollution enables to form and register motion activity signals from mollusk's shell valves, as well as automatically make a decision on deterioration of aquatic environment under investigation basing on a change in parameters of this motion activity, which is conditioned by the stress developing in the mollusk organism and connected with deterioration of water quality.

At the same time, using this equipment provides for gluing the lower shell valve of the test mollusk to the horizontally placed base in a position differing from that of the mollusk under its natural life conditions by a split between the shell valves oriented upwards, as well as its position between the base and elastic plate, which owing to mechanical contact and its own elastic properties exerts a rather significant pressure on the upper shell valve and, thus, prevents its opening. This can, first, cause the state of stress in this animal, which is not connected with a change in the quality of aquatic environment under investigation and can lead to a wrong decision-making about the quality of water under investigation. Second, the same reason can bring about a disease and even death of the test animal, which leads to higher cost and more complicated operation of the equipment for detecting aquatic environment pollution connected with the necessity to more frequently replace test animals in consequence of their disease or death.

In addition, using in this equipment for transmitting an electrical signal from the Hall probe or inductive sensor a rather long wire communication line does not protect this communication line against inevitable external interference inductions that distort the electrical signal of motion activity of the mollusk shell valves and can therefore lead to a wrong decision-making about the quality of aquatic environment under investigation.

By its structure, the closest to the biological environment monitoring system being the subject of this invention should be considered a computer-aided physiological monitoring system CAPMON (Depledge M. H., Andersen B. B. A computer-aided physiological monitoring system for continuous, long-term recording of cardiac activity in sample invertebrates.—Comp. Biochem. Physiol., Vol. 96A, 1990, No. 4, p.p. 473-477) that can be used to monitor aquatic environment and is based on non-invasive formation, registration and analysis of cardiac activity signals of crabs performing the function of test invertebrates. This known computer-aided physiological monitoring system chosen as the closest prototype contains eight shapers of a digital signal of cardiac activity, each containing series-connected cardiac activity sensor, amplifier, and analog-to-digital converter. The system also contains a computer with a printer and a hard-disk drive, and multiplexer whose input and output are connected, respectively, to the outputs of analog-to-digital converters of the shapers of a digital signal of cardiac activity_and to the computer input. Here, the cardiac activity sensor of each shaper of the digital signal of cardiac activity contains a hermetic casing made so that it can be placed and secured in a protection ring made with the possibility to be installed on the crab's carapace within its heart area, for example, with the help of an adhesive joint; a light-emitting diode placed inside the casing as an optical radiation source and made with the possibility of emitting optical radiation of near IR spectral range; a phototransistor placed inside the casing as an optical radiation receiver sensible to optical radiation of near IR spectral range; a wire line of communication with the power supply connected to a light-emitting diode; and a wire line of communication with the amplifier of the shaper of the digital signal of cardiac activity, which line is connected to the phototransistor.

This known computer-aided physiological monitoring system chosen as the closest prototype enables to form and register crabs' cardiac activity signals, and also automatically make a decision about the quality of aquatic environment under investigation, basing on a change of such a crabs' cardiac activity parameter as the heartbeat period, which is conditioned by the stress developing in their organism in connection with water quality deterioration.

Using for shaping an electrical signal in this known computer-aided physiological monitoring system chosen as the closest prototype a crabs' cardiac activity sensor containing an optical radiation source and an optical radiation receiver installed inside the hermetic casing separately from aquatic environment under investigation prevents the rise of instability of the electrical signal and the rise of noise accompanying it, including in the case of a significant electric conductivity of aquatic environment under investigation. This simplifies further processing of the formed electrical signal by the computer-aided physiological monitoring system and reduces probability of a wrong decision-making on the state of water under investigation.

For the same reason a change in electric conductivity of water under investigation does not influence the amplitude of the electrical signal formed by the crabs' cardiac activity sensor, which promotes reliable registration of the electrical signal by the computer-aided physiological monitoring system and lowers probability of a wrong decision-making about the quality of water under investigation. Moreover, when the electrical signal is processed, this excludes the necessity to use in the computer-aided physiological monitoring system an algorithmic compensation for a change in its amplitude caused by a change in water electric conductivity. This simplifies the structure and lowers the cost of the computer-aided physiological monitoring system and also simplifies its operation since this does not require regular calibration of this system using water with different electrical conductivity.

At the same time, the hermetic casing with the optical radiation source and optical radiation receiver placed in it that is used in the structure of the crabs' cardiac activity sensor incorporated in this computer-aided physiological monitoring system has rather significant mass and dimensions. Therefore, placing such a casing with an optical radiation source and optical radiation receiver inside it on the crab's carapace can, first, cause the state of stress in this animal not connected with a change of the quality of aquatic environment under investigation, but rather with the presence of a massive and sizeable foreign body on the carapace. As a result, when this known computer-aided physiological monitoring system processes an electrical signal formed by the sensor, a wrong decision may be made about the quality of water under investigation. Second, the same reason can cause a disease and even death of the test animal, which leads to higher cost and more complicated operation of the computer-aided physiological monitoring system chosen as the closest prototype in connection with the necessity to more frequently replace test animals in consequence of their disease or death.

In addition, using a wire line for communicating the optical radiation receiver of the crabs' cardiac activity sensor with the amplifier in this known computer-aided physiological monitoring system does not protect this communication line against inevitable external interference inductions that distort the electrical signal of crabs' cardiac activity and during the processing thereof can lead to making a wrong decision on the quality of aquatic environment under investigation.

Therefore, disadvantages of the known computer-aided physiological monitoring system chosen as the closest prototype are an insufficiently high reliability of environment monitoring and its high operating cost and complexity of operation.

DISCLOSURE OF THE INVENTION

The tasks for the group of inventions pertaining to the method of biological environment monitoring (versions) are to increase reliability of environment monitoring, widen functional potentials, and also cut down the cost and simplify the operation of the biological environment monitoring system.

The tasks of the invention pertaining to a system for implementing the applied—for method of biological environment monitoring are to increase reliability of environment monitoring and also cut down the cost and simplify the operation of the biological environment monitoring system.

Therefore, the tasks of the entire group of inventions are to increase reliability of environment monitoring, widen functional potentials, as well as reduce the cost and simplify the operation of the biological environment monitoring system.

According to this invention, the tasks set are solved, first, by that the method of biological environment monitoring including in accordance with the closest prototype:

placing a test invertebrate having a hard outer covering in the environment under investigation;
exposing the test invertebrate's heart area to optical radiation of IR spectral range;
receiving and converting the optical radiation reflected by the test invertebrate's heart to an electrical signal;
amplifying the electrical signal received;
converting its instantaneous values to digital codes;
feeding the obtained digital codes to a computer;
determining and memorizing with the help of the computer a preset-volume sample of values of the period of the electrical signal;
determining with the help of the computer a statistical characteristic of the sample of values of the electrical signal period;
comparing with the help of the computer the obtained statistical characteristic with the threshold value set for it; and
forming an ecological danger signal basing on the comparison results differs from the closest prototype in that exposing the test invertebrate to IR optical radiation is carried out with the help of a transmitting optical fibre with its output end placed on the test invertebrate's hard outer covering in its heart area and an optical radiation source mounted so that it can have optical contact with the input end of the transmitting optical fibre;

receiving the optical radiation reflected by the test invertebrate's heart is made with the help of a receiving optical fibre with its input end placed on the test invertebrate' hard outer covering within its heart area;

converting the optical radiation reflected by the test invertebrate's heart to an electrical signal is made with the help of the optical radiation receiver mounted so that it can have optical contact with the output end of the receiving optical fibre;

prior to determining the sample of values of the electrical signal period, computer-aided digital filtration of digital codes, which is matched to the shape and frequency of the electrical signal;

determining a sample dispersion as a statistical characteristic of the sample of values of the electrical signal period; and forming an ecological danger signal in case the threshold value exceeds of the obtained sample dispersion of values of the electrical signal period.

Here, exposing the test invertebrate to optical radiation and receiving the optical radiation reflected by the test invertebrate's heart is made, for example, with the help of the transmitting and receiving optical fibres mounted, respectively, with their output end and input end facing the same side and placed relative to each other at a distance satisfying the inequality $$(\pi d^2 P)^{0.07} - 2.2(1/(\pi d^2 P))^{0.02} \leq R \leq (\pi d^2 P)^{0.07} + 2.2(1/(\pi d^2 P))^{0.02},$$

where R—distance between the output end of the transmitting optical fibre and the input end of the receiving optical fibre, mm; P—output power of the optical radiation source, mW; d—diameter of the transmitting optical fibre or receiving optical fibre, μm.

During digital filtration of digital codes the estimates of digital codes are determined which correspond to instantaneous values of the electrical signal with zero constant component at the instants of time $t_n = n\Delta t$ (n=m, m+1, m+2, ... ), e.g. according to the expression $$\hat{x}_n = 1/(\pi \Delta t) \sum_{i=n-m+1}^{n+m} x_i (\sin(2\pi(f_0 + \Delta f)(t_i - t_n)) - \sin(2\pi(f_0 - \Delta f)(t_i - t_n)))/(t_i - t_n),$$

where Δt—interval of discreteness of electrical signal quantization in time during conversion of its instantaneous values to digital codes; 2m—number of digital codes used during filtration; $f_0$—expected heartbeat frequency in the test invertebrate; Δf—digital filter's pass half-band, $\Delta f = (0.1-0.8)f_0$.

Also a sample mean value can be determined as a statistical characteristic of the sample of values of the electrical signal period.

In this case, an ecological danger signal is formed, should the threshold value exceed the product of the sample mean value by the sample dispersion of values of the electrical signal period.

In this case, the expected heartbeat frequency $f_0$ in the test invertebrate is determined as a value inverse to the sample mean value of the electrical signal period.

The volume of the sample of values of the electrical signal period is set within the limits of 30 to 1000.

According to this invention, exposing the test invertebrate to IR optical radiation in the biological environment monitoring method with the help of a transmitting optical fibre whose output end is placed on the test invertebrate's hard outer covering within its heart area, and an optical radiation source installed so that it can have optical contact with the input end of the transmitting optical fibre, as well as receiving the optical radiation reflected by the test invertebrate's heart with the help of a receiving optical fibre whose input end is located on the test invertebrate's hard outer covering within its heart area, and converting the optical radiation reflected by the test invertebrate's heat to an electrical signal with the help of an optical radiation receiver installed so that it can have optical contact with the output end of the receiving optical fibre ensures higher reliability of environment monitoring and also lower cost and simplification of operation of the biological environment monitoring system realizing this method. This assertion is confirmed by the following considerations.

First, this enables to place the optical radiation source and optical radiation receiver not in the casing mounted on the test invertebrate's body as is provided for implementation of the method chosen as the closest prototype, but in the immediate vicinity of the equipment for amplification and processing of the cardiac activity signal, which ensures lower mass and dimensions of the elements placed on the test invertebrate's body. Such refusal to place the optical radiation source and optical radiation receiver inside the casing makes it possible to use a non-hermetic casing of a fairly simple structure, e.g. in the form of a hollow cylinder, which leads to an even lesser mass and dimensions of the elements placed on the test invertebrate's body. Lesser mass and dimensions of the elements placed on the test invertebrate's body, on the one hand, lowers probability that this animal develops the state of stress connected not with a change in the quality of environment under investigation, but with the presence of a foreign body on it. This results in lower probability of making a wrong decision on the quality of environment under investigation. On the other hand, the lesser mass and dimensions of the elements placed on the test invertebrate's body reduces probability of a disease or death of the test animal, which leads to lower cost and simplified operation of the biological environment monitoring system realizing this method thanks to no need to frequently replace test animals.

Second, these above listed distinctive features of the method applied for ensure, while implementing it, absolute protection of the communication line in the form of a receiving optical fibre against the impact of electromagnetic fields, which prevents the rise of any external electromagnetic inductions in it. This impedes a distortion of the electrical signal of cardiac activity being formed, which considerably reduces probability of making a wrong decision about the quality of environment under investigation.

Higher environment monitoring reliability while exercising this biological environment monitoring method also ensures the use, prior to determining the preset-volume sample of values the period of the electrical signal chosen e.g. within the limits of 30-1000, digital filtration of digital codes which is matched to the shape and frequency of the electrical signal and is made with the help of a computer, for example, by determining the estimates of digital codes corresponding to instantaneous values of the electrical signal with zero constant component at the instants of time $t_n = n\Delta t$ (n=m, m+1, m+2, ...) according to the expression $$\hat{x}_n = 1/(\pi \Delta t) \sum_{i=n-m+1}^{n+m} x_i (\sin(2\pi(f_0 + \Delta f)(t_i - t_n)) - \sin(2\pi(f_0 - \Delta f)(t_i - t_n)))/(t_i - t_n),$$

where $\Delta t$—interval of discreteness of electrical signal quantization in time during the conversion of its instantaneous values to digital codes; 2m—number of digital codes used during filtration; $f_0$—expected test invertebrate's heartbeat frequency; $\Delta f$—digital filter's pass half-band, $\Delta f(0.1\text{-}0.8)f_0$.

As noted above, the electrical signal of cardiac activity formed by the optical radiation receiver, first, is accompanied by a sizeable constant component and, second, has a rather complex a priori unknown form that is unstable in time due to movements of the test animal. These reasons account for serious errors during direct determination of the electrical signal period and, consequently, the test animal's heartbeat period. Digital filtration used in this method and performed before determining the electrical signal period enables to obtain estimates of digital codes corresponding to instantaneous values of the electrical signal devoid of a constant component and having a sinusoidal shape and a period equal to the period of the electrical signal obtained with the help of the optical radiation receiver.

First, this results in a simpler procedure of determining the electrical signal period by a computer. In this case such procedure comes to detecting two pairs of estimates of digital codes closest by the time of obtaining them for two instants of time differing by the value of interval $\Delta t$ of discreteness of electrical signal quantization in time when converting its instantaneous values to digital codes and having different signs, and to determining the difference between the values of time instants for which these two pairs were obtained. Second, this decreases an error in determining the electrical signal period, which in this case does not exceed the value of interval $\Delta t$ of discreteness of electrical signal quantization in time during converting its instantaneous values to digital codes. Decreasing the error in determining the electrical signal period and, consequently, the test invertebrate's heartbeat period leads to a higher environment monitoring reliability.

Determining, while exercising the biological environment monitoring method being the subject of this invention, a sample dispersion as a statistical characteristic of the sample of the period values of an electric signal, the preset volume of the sample being chosen e.g. within 30-1000, and forming an ecological danger signal in case the threshold value exceeds the obtained sample dispersion of values of the electrical signal period, ensures higher environment monitoring reliability, widening of functional potentials, as well as lower cost and simplification of operation of the biological environment monitoring system realizing the present method. This is confirmed by the following considerations.

Experimental research conducted by the authors of this invention in laboratory and full-scale conditions showed that during registration of the heartbeat period of invertebrates with a hard outer covering in quiet state a rather wide spread of heartbeat period values obtained is observed, while in the state of stress a deviation of the obtained values of the heartbeat period from its sample mean value substantially decreases. Thus, for example, during registration of invertebrates' cardiac activity parameters the authors of this invention found that the initial stage of transition from quiet state to the state of stress in various conventionally healthy crayfish species is accompanied by a decrease of the obtained sample dispersion of the heartbeat period by a factor of 100-10000.

Here, experimental research conducted by the authors of this invention in laboratory and full-scale conditions to study invertebrates' cardiac activity did not detect at least one conventionally healthy individual invertebrate with a hard outer covering in which the initial stress stage, i.e. an alarm reaction was not accompanied by a fairly noticeable decrease of the sample dispersion_of the heartbeat period.

For that reason, forming an ecological danger signal when the threshold value exceeds the obtained sample dispersion of the electrical signal period, this dispersion being equal to the sample dispersion of the heartbeat period, first, ensures higher environment monitoring reliability. Second, this brings to no need to preliminarily select animals for use as test_organisms, which cuts down the cost and simplifies operation of the biological environment monitoring system realizing this method.

The aforementioned experimental research conducted by the authors of this invention to study cardiac activity of invertebrates with a hard outer covering also showed that in shell mollusks living both in aquatic environment and on land the sample dispersion of the heartbeat period at the initial stage of their transition to the state of stress significantly reduces as well. Thus, for instance, in vine snails and giant African snails achatines the sample dispersion of the heartbeat period reduces by a factor of 100-5000.

This widens functional potentials and scope of possible application of this method not only for monitoring the state of aquatic environment and bottom sediments, but also for monitoring the state of air and soil using, e.g. land-living shell mollusks as test animals.

In opinion of the authors of this invention, the best technical result while implementing this method is achieved when, besides the sample dispersion, a sample mean value is additionally determined as a statistical characteristic of the preset-volume sample of values of the period of the electrical signal, this preset volume being chosen, for example, within the limits of 30 to 1000, and then an ecological danger signal is formed, should the threshold value exceed the product of the sample mean by the sample dispersion of values of the electrical signal period, which ensures higher sensitivity of the system realizing this method to ecologically dangerous substances entering the environment. As noted above, this happens because in all invertebrates with a hard outer covering the state of stress is accompanied by a considerable decrease of the sample dispersion of the heartbeat period and in some of their species and in overwhelming majority of individuals within these species, by a decrease of the sample mean_value of the heartbeat period. Owing to this, the product of the sample mean by the sample_dispersion, in which both cofactors decrease, is subject to a more considerable decrease, which impedes possible missing in registration by the system of the state of stress in test animals caused by a breach of ecological situation and, therefore, helps increase environment monitoring reliability.

From the viewpoint of minimizing the probability of a wrong decision-making about the quality of environment under investigation, the best technical result during the implementation of this method is achieved when the exposure of a test invertebrate to optical radiation and reception of optical radiation reflected by the test invertebrate's heart is carried out with the help of the transmitting and receiving optical fibres secured so that, respectively, their output end and input end face one side and are placed relative one another at a distance satisfying the inequality $$(\pi d^2 P)^{0.07} - 2.2(1/(\pi d^2 P))^{0.02} \leq R \leq (\pi d^2 P)^{0.07} + 2.2(1/(\pi d^2 P))^{0.02},$$

where R—distance between the output end of the transmitting optical fibre and input end of the receiving optical fibre, mm; P—output power of the optical radiation source, mW; d—diameter of the transmitting optical fibre or receiving optical fibre, μm. A confirmation to this fact will be given below when the system to implement the method applied for is discussed.

Second, the tasks set are solved according to this invention also by that the method of biological environment monitoring including in accordance with the closest prototype:

placing the test invertebrate with a hard outer covering in the environment under investigation;
exposing the test invertebrate's heart area to optical radiation of IR spectral range;
receiving and converting the optical radiation reflected by the test invertebrate's heart to an electrical signal;
amplifying the electric signal received;
converting its instantaneous values to digital codes;
entering the codes to a computer;
determining and memorizing with the help of the computer a preset-volume sample of values of the period of the electrical signal;
determining with the help of the computer a statistical characteristic for the sample of values of the electrical signal period;
comparing with the help of the computer the obtained statistical characteristic with its established threshold value; and
forming an ecological danger signal basing on the comparison result, differs from the closest prototype in that
exposing the test invertebrate to IR optical radiation is carried out with the help of a transmitting optical fibre with its output end placed on the test invertebrate's hard outer covering within its heart area, and an optical radiation source installed so that it can have optical contact with the input end of the transmitting optical fibre;
receiving the optical radiation reflected by the test invertebrate's heart is carried out with the help of a receiving optical fibre whose input end is placed on the test invertebrate's hard outer covering within its heart area;
converting the optical radiation reflected by the test invertebrate's heart to an electrical signal is made with the help of an optical radiation receiver installed so that it can have optical contact with the output end of the receiving optical fibre;
prior to determining a sample of values of the electrical signal period, the computer-aided digital filtration of digital codes that is matched to the electrical signal shape and frequency is made;

the arithmetical mean of difference moduli for each two sample values of the electrical signal period closest by the time of obtaining is determined as a statistical characteristic of the sample of values of the electrical signal period;

and an ecological danger signal is formed in case the threshold value exceeds the obtained arithmetical mean of difference moduli for each two sample values of the electrical signal period closest by the time of obtaining.

In this case, exposing the test invertebrate to optical radiation and receiving the optical radiation reflected by the test invertebrate's heart is carried out with the help of the transmitting and receiving optical fibres secured, respectively, so that their output end and input end face the same side and are positioned relative to each other at a distance satisfying the inequality $$(\pi d^2 P)^{0.07} - 2.2(1/(\pi d^2 P))^{0.02} \leq R \leq (\pi d^2 P)^{0.07} + 2.2(1/(\pi d^2 P))^{0.02},$$

where R—distance between the output end of the transmitting optical fibre and input end of the receiving optical fibre, mm; P—output power of the optical radiation source, mW; d—diameter of the transmitting optical fibre or receiving optical fibre, μm.

During digital filtration of digital codes the estimates of digital codes are determined that correspond to instantaneous values of the electrical signal with zero constant component at the instants of time $t_n = n\Delta t$ ($n=m, m+1, m+2, \ldots$) according to the expression $$\hat{x}_n = 1/(\pi \Delta t) \sum_{i=n-m+1}^{n+m} x_i (\sin(2\pi(f_0 + \Delta f)(t_i - t_n)) - \sin(2\pi(f_0 - \Delta f)(t_i - t_n)))/(t_i - t_n),$$

where $\Delta t$—interval of discreteness of electrical signal quantization in time when its instantaneous values are converted to digital codes; 2m—number of digital codes used during filtration; $f_0$—expected heartbeat frequency in the test invertebrate; $\Delta f$—digital filter's pass half-band, $\Delta f = (0.1 - 0.8) f_0$.

Also a sample mean value can be determined as a statistical characteristic for the sample of values of the electrical signal period.

In this case an ecological danger signal is formed, should the threshold value exceed the product of the sample mean by the square arithmetical mean of difference moduli for each two sample values of the electrical signal period closest by the time of obtaining.

In this case the expected heartbeat frequency $f_0$ in the test invertebrate is determined as a value inverse to the sample mean value of the electrical signal period.

The volume of the sample of values of the electrical signal period is set within the limits of 30 to 1000.

Using in the biological environment monitoring method being the subject of this invention the exposure of a test invertebrate to IR optical radiation with the help of a transmitting optical fibre with its output end placed on the test invertebrate's hard outer covering within its heart area and an optical radiation source installed so that it can have optical contact with the input end of the transmitting optical fibre, and also the reception of optical radiation reflected by the test invertebrate's heart with the help of a receiving optical fibre whose input end is placed on the test invertebrate's hard outer covering within its heart area, and the conversion of optical radiation reflected by the test invertebrate's heart to an electrical signal with the help of an optical radiation receiver secured so that it can have optical contact with the output end of the receiving optical fibre ensures higher environment monitoring reliability and also lower cost and simplification of operation of the biological environment monitoring system realizing this method. This assertion is confirmed by the following considerations.

First, this enables to place an optical radiation source and optical radiation receiver not in the casing installed on the test invertebrate's body as is provided for while implementing the prototype-closest method, but rather in the immediate proximity to the equipment for amplifying and processing the cardiac activity signal, which ensures lesser mass and dimensions of elements placed on the test invertebrate's body. Such refusal to place the optical radiation source and optical radiation receiver inside the casing makes it possible to use a non-hermetic casing of a rather simple structure, for example, in the form of a hollow cylinder, which leads to an even greater decrease of the mass and dimensions of elements placed on the test invertebrate's body. On the one hand, decreasing the mass and dimensions of elements placed on the test invertebrate's body reduces probability that this animal gets into the state of stress connected not with a change in the quality of environment under investigation, but with the presence of a foreign body on it, which results in lower probability of making a wrong decision about the quality of environment under investigation. On the other hand, decreasing the mass and dimensions of elements placed on the test invertebrate's body reduces probability of a disease or death of the test animal, which leads to lower cost and simplifies operation of the biological environment monitoring system realizing this method owing to no need to frequently replace test animals.

Second, the same aforementioned distinctive features of the method being applied for ensure while implementing it an absolute protection of the communication line in the form of a receiving optical fibre against the impact of electromagnetic fields, which prevents the rise therein of any outside electromagnetic inductions. This impedes a distortion of the electrical signal of cardiac activity being formed, which greatly reduces probability of making a wrong decision about the quality of environment under investigation.

Increasing environment monitoring reliability when exercising this biological environment monitoring method also ensures using, prior to determining a preset-volume sample of values of the period of an electrical signal, this volume being chosen e.g. within the limits of 30 to 1000, digital filtration of digital codes that is matched to the shape and frequency of the electrical signal and is made with the help of a computer, for instance, by way of determining the estimates of digital codes corresponding to instantaneous values of the electric signal with zero constant component at the instants of time $t_n = n\Delta t$ (n=m, m+1, m+2, . . . ) according to the expression $$\hat{x}_n = 1/(\pi \Delta t) \sum_{i=n-m+1}^{n+m} x_i (\sin(2\pi(f_0 + \Delta f)(t_i - t_n)) - \sin(2\pi(f_0 - \Delta f)(t_i - t_n)))/(t_i - t_n),$$

where $\Delta t$—interval of discreteness of electrical signal quantization in time when instantaneous values of the signal are converted to digital codes; 2m—number of digital codes used during filtration; $f_0$—expected heartbeat frequency in the test invertebrate; $\Delta f$—digital filter's pass half-band, $\Delta f=(0.1-0.8)f_0$.

As was noted above, an electrical signal of cardiac activity being formed by the optical radiation receiver is, first, accompanied by a sizeable constant component and, second, has a rather complex a priori unknown form unstable in time due to movements of the test animal. These reasons lead to serious errors during direct determination of the electrical signal period and, hence, heartbeat period in the test animal. Digital filtration used in this method and carried out before determining sample values of the electrical signal period enables to obtain estimates of digital codes corresponding to instantaneous values of the electrical signal that has no constant component, is of a sinusoidal shape and has a period equal to that of the electrical signal actually received with the help of the optical radiation receiver.

First, this results in simplification of the procedure of determining the electrical signal period by a computer. In this case, such procedure comes to detecting pairs of estimates of digital codes that are closest by the time of their obtaining and are received for two instants of time differing by the value of interval $\Delta t$ of discreteness of electrical signal quantization in time when instantaneous values of the signal are converted to digital codes, and have different signs in this case; and to determining the difference of values of the instants of time for which these two pairs were obtained. Second, this decreases the error of determining the electrical signal period, in which case it will not exceed the value of interval $\Delta t$ of discreteness of electrical signal quantization in time when instantaneous values of the signal are converted to digital codes. Lower error in determining the electrical signal period and, hence, the test invertebrate's heartbeat period enhances reliability of environment monitoring.

Determining, while exercising the biological environment monitoring method being the subject of this invention, the arithmetical mean of difference moduli for each two sample values of the electrical signal period closest by the time of obtaining and used as a statistical characteristic of the preset-volume sample of values of the period of the electrical signal, this volume being chosen, for example, within the limits of 30 to 1000; and forming an ecological danger signal, should the threshold value exceed the obtained arithmetical mean for difference moduli of each two sample values of the electric signal period closest by the time of obtaining improves reliability of environment monitoring, ensures its wider functional potentials and also lower cost and simpler operation of the biological environment monitoring system realizing the present method. This is confirmed by the following considerations.

Experimental research conducted by the authors of this invention in laboratory and full-scale conditions showed that during registration of the heartbeat period of invertebrates with a hard outer covering in quiet state there is a fairly wide spread of the heartbeat period values obtained, whereas in the state of stress the deviation of obtained values of heartbeat period from its sample value essentially decreases. Thus, for instance, when registering invertebrates' cardiac activity parameters, the authors of this invention found that the initial stage of transition from quiet state to stress state in conventionally healthy crayfish of different species is accompanied by a decrease of the arithmetical mean obtained for difference moduli of each two sample heartbeat-period values, closest by the time of obtaining, by a factor of 10-100.

Experimental research conducted by the authors of this invention in laboratory and full-scale conditions to study invertebrates' cardiac activity did not detect at least one conventionally healthy individual invertebrate with a hard outer covering in which the initial stage of stress, i.e. alarm reaction, was not accompanied by a significant decrease of the arithmetical mean of difference moduli for each two sample values of the heartbeat period closest by the time of obtaining.

Therefore, forming an ecological danger signal in case the threshold value exceeds the arithmetical mean obtained for difference moduli of each two sample values of the electrical signal period closest by the time of obtaining, this arithmetical mean being equal to the arithmetical mean of difference moduli of each two sample values of the heartbeat period that are closest by the time of obtaining, first, ensures higher reliability of environment monitoring. Second, this excludes the need to preliminarily select animals for use as test organisms, which ensures lower cost and simpler operation of the biological environment monitoring system realizing the present method.

The aforementioned experimental research conducted by the authors of this invention to study cardiac activity of invertebrates with a hard outer covering also showed that in shell mollusks living both in aquatic environment and on land the arithmetical mean of difference moduli for each two sample values of the heartbeat period closest by the time of obtaining also significantly decreases at the initial stage of their transition to the state of stress. Thus, for example, in vine snails and giant African snails achatines the arithmetical mean of difference moduli for each two sample values of the heartbeat period, closest by the time of obtaining, decreases by a factor of 10 to 80.

This widens functional potentials and scope of possible application of this method enabling to use it not only for monitoring the state of aquatic environment and bottom sediments, but also for monitoring the state of air and soil using, for example, shell mollusks living on land as test animals.

In opinion of the authors of this invention, the best technical result while implementing this method is achieved in the case if, besides the arithmetical mean of difference moduli for each two sample values of the electrical signal period closest by the time of obtaining held as a statistical characteristic for the preset-volume sample of values of the period of the electrical signal, this volume being chosen, e.g. within the limits of 30 to 1000, a sample mean value is additionally determined and an ecological danger signal is formed in case the threshold value exceeds the product of the sample mean by square arithmetical mean of difference moduli for each two sample values of the electrical signal period that are closest by the time of obtaining. In this case, also provided is higher sensitivity of the system realizing this method to ecologically dangerous substances getting into the environment.

As was noted above, this happens because in all invertebrates with a hard outer covering the state of stress is accompanied by a considerable decrease of the arithmetical mean of difference moduli for each two sample values of the heartbeat period closest by the time of obtaining, while in some of their species and in overwhelming majority of individuals within these species also by a decrease of the sample mean value of the heartbeat period. Owing to this, the product of the sample mean by square arithmetical mean of difference moduli for each two sample values of the heartbeat period closest by the time of obtaining, in which product both cofactors decrease, is subject to a more essential decrease, which impedes possible failure of registration by the system of test animals' state of stress caused by a breach of ecological situation and, therefore, helps increase reliability of environment monitoring.

From the viewpoint of minimizing the probability of making a wrong decision about the quality of environment under investigation, the best technical result while implementing this method is achieved when exposing the test invertebrate to optical radiation and receiving the optical radiation reflected by the test invertebrate's heart is carried out with the help of the transmitting and receiving optical fibres secured so that their, respectively, output end and input end face one side and are positioned relative to each other at a distance satisfying the inequality $$(\pi d^2 P)^{0.07} - 2.2(1/(\pi d^2 P))^{0.02} \leq R \leq (\pi d^2 P)^{0.07} + 2.2(1/(\pi d^2 P))^{0.02},$$

where R—distance between the output end of the transmitting optical fibre and input end of the receiving optical fibre, mm; P—output power of the optical radiation source, mW; d—diameter of the transmitting optical fibre or receiving optical fibre, μm. A confirmation to this fact will be given below where the system for implementing the method applied for is discussed.

Third, according to this invention, the tasks set are also solved by that the biological environment monitoring system containing, pursuant to the closest prototype, a computer and at least one shaper of a digital signal of cardiac activity in the form of series-connected cardiac activity sensor including a casing with an element for installing it on the body of the test invertebrate with a hard outer covering; an optical radiation source and optical radiation receiver; and amplifier whose input is connected to the output of the optical radiation receiver; and an analog-to-digital converter whose output is connected to the computer input, differs from the closest prototype in that its cardiac activity sensor is equipped with the transmitting and receiving optical fibres, the input end of the transmitting optical fibre and output end of the receiving optical fibre are installed so they can have optical contact, respectively, with the optical radiation source and optical radiation receiver, while the output end of the transmitting optical fibre and input end of the receiving optical fibre face one side and are positioned within the casing at a distance satisfying the inequality $$(\pi d^2 P)^{0.07} - 2.2(1/(\pi d^2 P))^{0.02} \leq R \leq (\pi d^2 P)^{0.07} + 2.2(1/(\pi d^2 P))^{0.02},$$

where R—distance between the output end of the transmitting optical fibre and input end of the receiving optical fibre, mm; P—output power of the optical radiation source, mW; d—diameter of the transmitting optical fibre or receiving optical fibre, μm.

As an optical radiation source for the cardiac activity sensor there can be used a semiconductor laser made so that it can emit optical radiation of IR spectral range or a light-emitting diode that can emit optical radiation of IR spectral range; a photodiode sensitive to IR optical radiation can be used as an optical radiation receiver for the cardiac activity sensor; the casing of the cardiac activity sensor can be made as a hollow cylinder; and the element for installing on the test invertebrate's body can be made as a hollow cylinder enclosing the casing and equipped with two lobes and a fixing screw.

Higher reliability of environment monitoring, and also lower cost and simpler operation of the biological environment monitoring system being the subject of this invention, is provided by equipping its cardiac activity sensor with a transmitting and receiving optical fibre when the input end of the transmitting optical fibre and output end of the receiving optical fibre are installed with the possibility of optical contact, respectively, with the optical radiation source and optical radiation receiver, while the output end of the transmitting optical fibre and input end of the receiving optical fibre face one side and are positioned within the casing at a distance satisfying the inequality $$(\pi d^2 P)^{0.07} - 2.2(1/(\pi d^2 P))^{0.02} \leq R \leq (\pi d^2 P)^{0.07} + 2.2(1/(\pi d^2 P))^{0.02},$$

where R—distance between the output end of the transmitting optical fibre and input end of the receiving optical fibre expressed in millimeters; P—output power of the optical radiation source expressed in milliwatts; d—diameter of the transmitting optical fibre or receiving optical fibre expressed in micrometers. This assertion is confirmed by the following considerations.

First, the above-listed distinctive features inherent in the biological environment monitoring system applied for enable to place the optical radiation source and optical radiation receiver not in the casing set up on the test invertebrate's body as is provided for in the closest-prototype system, but in immediate proximity of the equipment for amplifying and processing the cardiac activity signal, which ensures lesser mass and dimensions of elements placed on the test invertebrate's body. Such refusal to place the optical radiation source and optical radiation receiver inside the casing makes it possible to use a non-hermetic casing of a rather simple structure, for example, in the form of a hollow cylinder, which leads to an even greater decrease of the mass and dimensions of elements placed on the test invertebrate's body. On the one hand, lesser mass and dimensions of elements placed on the test invertebrate's body reduces probability that this animal will fall into the state of stress connected not with a change in the quality of environment under investigation, but rather with the presence of a foreign body on it. This results in lower probability of making a wrong decision on the quality of environment under investigation. On the other hand, reducing the mass and dimensions of elements placed on the test invertebrate's body lowers probability that the test animal will develop a disease or dies, which leads to lower cost and simpler operation of the biological environment monitoring system thanks to no need to frequently replace test animals.

Second, these same aforementioned distinctive features of the biological environment monitoring system applied for ensures absolute protection of the communication line in the form of a receiving optical fibre against the impact of electromagnetic fields, which prevents the appearance in it of any external electromagnetic inductions. This hampers a distortion of the electrical signal of cardiac activity being formed, which greatly lowers probability of making a wrong decision on the quality of environment under investigation.

Experimental research conducted by the authors of this invention showed that when output power of the optical radiation source and diameters of the transmitting and receiving fibres are invariable, the electrical signal of cardiac activity being formed greatly depends on relative position of the output end of the transmitting optical fibre and input end of the receiving optical fibre. Here, for the output power value of the employed optical radiation source and chosen value of diameters of the transmitting and receiving optical fibres used there exists a rather definite range of values for the distance between the output end of the transmitting optical fibre and input end of the receiving optical fibre within which an electrical signal of cardiac activity of such a quality is obtained which enables to determine its period with a required accuracy during subsequent processing thereof.

As a result of this research the authors obtained the above presented empirical expression in the form of a double inequality, which determines the range of possible values for distance R between the output end of the transmitting optical fibre and input end of the receiving optical fibre depending on the value of output power P of the optical radiation source used and on the values of diameters d of the transmitting and receiving fibres used. Since the above inequality is of empirical nature, then in order to determine numerical values of the limits of said range expressed in millimeters for possible values of distance R between the output end of the transmitting optical fibre and input end of the receiving optical fibre, it is necessary to introduce into said inequality the numerical value of output power P of the used optical radiation source expressed in milliwatts and the numerical value of diameter d of the transmitting optical fibre and receiving optical fibre expressed in micrometers.

When choosing the distance between the output end of the transmitting optical fibre and input end of the receiving optical fibre outside the limits of this range of possible values set by the above inequality, the formed electrical signal of cardiac activity cannot be processed and its period determined for the following reasons.

If the distance between the output end of the transmitting optical fibre and input end of the receiving optical fibre on which they are positioned is by its value chosen smaller than values lying within said range, there takes place an excessive exposure of the input end of the receiving optical fibre to optical radiation reflected and scattered by the invertebrate's hard outer covering and its internal organs, but heart. This causes saturation of the optical radiation receiver so that the electrical signal ceases to depend on the invertebrate's heartbeat. If the distance between the output end of the transmitting optical fibre and input end of the receiving optical fibre on which they are positioned exceeds by its value the values lying within said range, the light flow of optical radiation reflected by the invertebrate's heart and coming to the input end will prove insufficient for detecting an electrical signal of cardiac activity from noises and for determining its period.

The above noted testifies to the solution of the aforementioned tasks declared for this invention thanks to that the method of biological environment monitoring (versions) and the system for its implementation applied for have the above-listed distinctive features.

VERSION OF EMBODIMENT OF THE INVENTION

Figure 1:
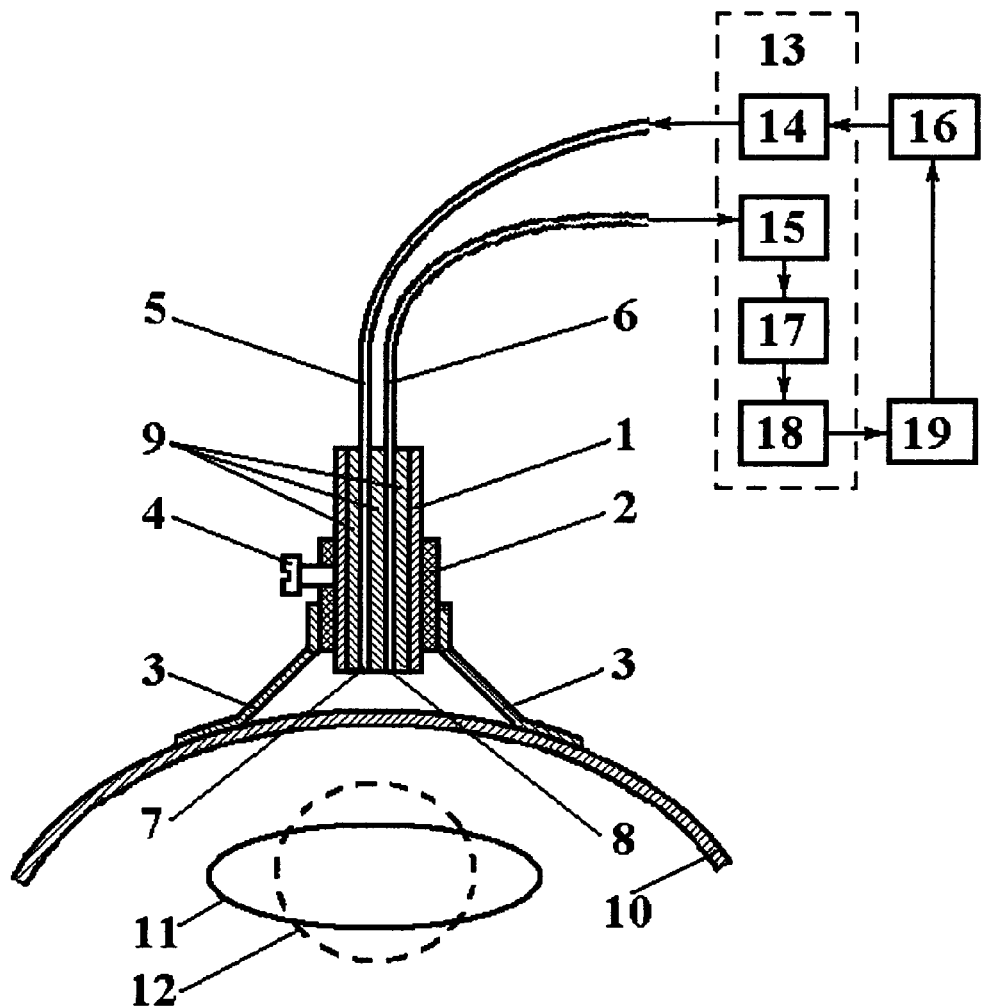
FIG. 1 shows a cross-section, of the casing and element for installing a cardiac activity sensor on the test invertebrate's body, as well as a circuit block diagram of the biological environment monitoring system realizing this method, where 1—casing, 2—cylinder of the installing element, 3—lobe of the installing element, 4—fixing screw, 5—transmitting optical fibre, 6—receiving optical fibre, 7—output end, 8—input end, 9—element for fixing the fibres, 10—test animal's outer covering, 11—test animal's heart during diastole period, 12—test animal's heart during systole period, 13—shaper of a digital signal of cardiac activity, 14—optical radiation source, 15—optical radiation receiver, 16—power supply for the optical radiation source, 17—amplifier, 18—analog-to-digital converter, and 19—computer.

The biological environment monitoring system being one of subjects of this invention and enabling to implement both versions of the method of biological environment monitoring applied for contains (see FIG. 1) a computer 19, power supply 16 for the optical radiation source, at least one shaper 13 of a digital signal of cardiac activity and at least one cardiac activity sensor.

The cardiac activity sensor contains an optical radiation source 14, e.g. a semiconductor laser or light-emitting diode made so that both can emit optical radiation of near infrared spectral range, an optical radiation receiver 15, e.g. a photodiode sensitive to optical radiation of nearest IR spectral range, a transmitting optical fibre 5 and receiving optical fibre 6. The input end of transmitting optical fibre 5 and output end of receiving optical fibre 6 are installed with the possibility of having optical contact, respectively, with optical radiation source 14 and optical radiation receiver 15 via optical fibre connectors (not shown in the figures), e.g. of ST or FC brand. As optical radiation source 14 there can be used a semiconductor laser or light-emitting diode having an output power of 5 to 300 mW, e.g. ILPN-109M-type semiconductor laser emitting optical radiation of 30 mW in power and wavelength of 0.80-0.86 μm. As an optical radiation receiver 15 in this case the use can be made of a photodiode, e.g. FD-290 type, sensitive to optical radiation of this wavelength range. Optical fibres with a diameter of 50 to 300 μm, for example, optical fibres of 50 μm in diameter can be used as transmitting optical fibre 5 and receiving optical fibre 6.

The cardiac activity sensor also contains a casing 1 made, for example, as a hollow cylinder, and an element for installing on the test invertebrate's body. The element for installing on the test invertebrate's body includes a hollow cylinder 2 of the installing element enclosing casing 1, two lobes 3 of the installing element whose shape and location correspond to the shape of the test animal's outer covering 10 at the place of supposed installation of the sensor within heart area, and a fixing screw 4 inserted in a threaded hole made in cylinder 2 of the installing element. Casing 1, cylinder 2 of the installing element and lobes 3 of the installing element are made from metal resistant to corrosion or from a polymer material. Output end 7 of transmitting optical fibre 5 and input end 8 of receiving optical fibre 6 facing the same side towards the test animal's outer covering 10 are placed in casing 1 and secured within it by element 9 for fixing the fibres made, for example, from hardened epoxy adhesive. Output end 7 and input end 8 are positioned within casing 1 at a distance satisfying the inequality $$(\pi d^2 P)^{0.07} - 2.2(1/(\pi d^2 P))^{0.02} \leq R \leq (\pi d^2 P)^{0.07} + 2.2(1/(\pi d^2 P))^{0.02},$$

where R—distance between output end 7 of transmitting optical fibre 5 and input end 8 of receiving optical fibre 6 expressed in millimeters, P—output power of optical radiation source 14 expressed in milliwatts, d—diameter of transmitting optical fibre 5 and receiving optical fibre 6 expressed in micrometers.

Thus, e.g. for experimental models of the biological environment monitoring system created and tested by the authors of this invention at output power P of the used optical radiation source equal to 30 mW and diameters d the used transmitting and receiving optical fibres 5 and 6 equal to 50 μm, the range of possible values of distance R between output end 7 of transmitting optical fibre 5 and input end 8 of receiving optical fibre 6 lies within the limits of approximately 1 to 5 mm. From the viewpoint of the quality of an electrical signal being formed, the best technical result here is achieved at the value of distance R between output end 7 of transmitting optical fibre 5 and input end 8 of receiving optical fibre 6 equal to about 3 mm.

Shaper 13 of a digital signal of cardiac activity contains optical radiation source 14 incorporated into the above-described cardiac activity sensor and connected to the output of power supply 16 of the optical radiation source, and optical radiation receiver 15 incorporated into the above-described cardiac activity sensor in series with amplifier 17 and analog-to-digital converter 18 connected to the input of computer 19. As computer 19 there can be used a personal computer equipped with a software enabling to make digital filtration of digital codes, which is matched to the shape and frequency of the electrical signal of cardiac activity, and to compare digital codes, as well as calculate basic statistical characteristics for the sample of vales of the electrical signal period.

Figure 2:
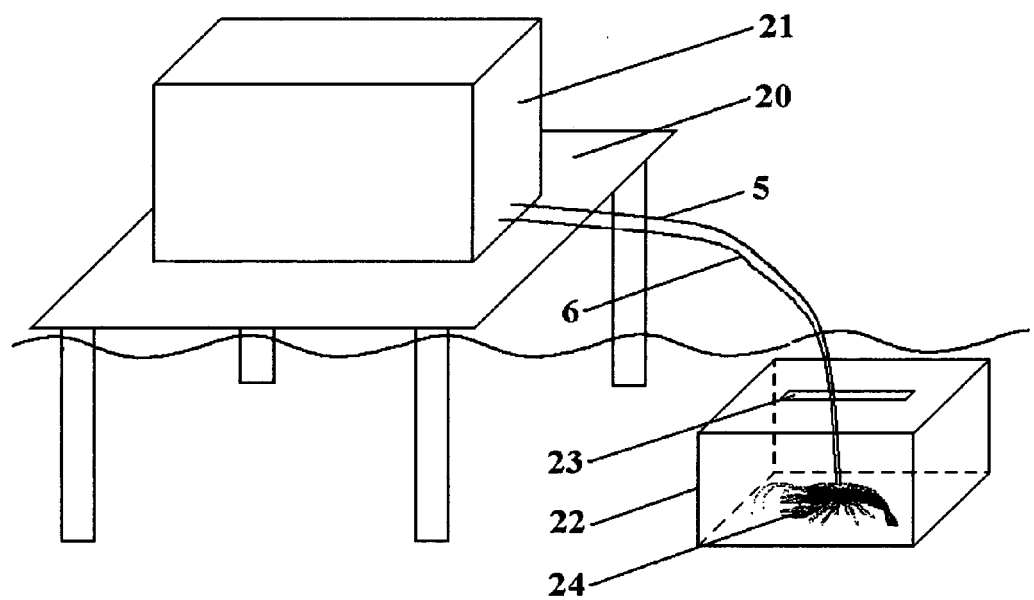
FIG. 2 shows a possible version of arranging the biological environment monitoring system in the case it is used to monitor aquatic environment of a water body, where 20—stage, 21—container for equipment, 22—cage for the animal, 23—slit for optical fibres, and 24—test animal.
Figure 3:
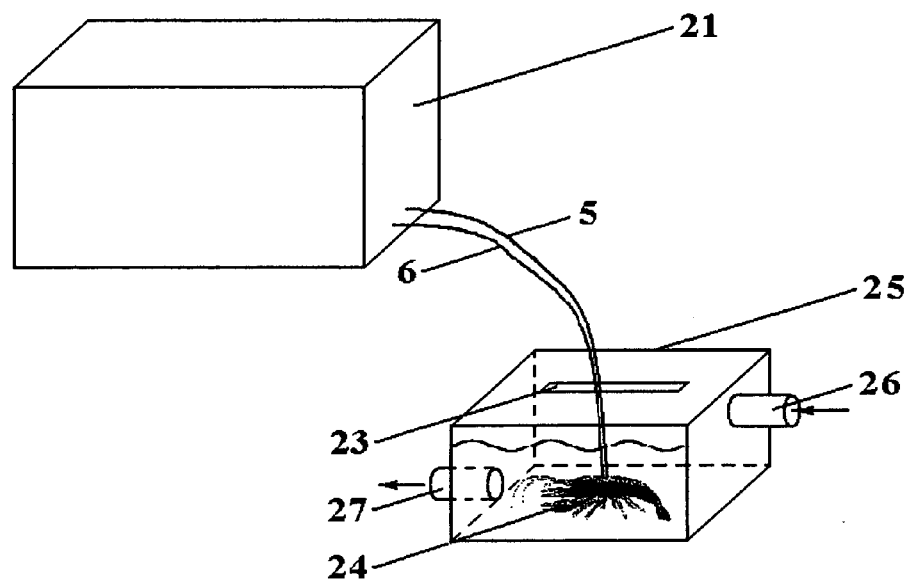
FIG. 3 shows a possible version of arranging the biological environment monitoring system in the case it is used to monitor the quality of water at water-treatment intake stations, where 25—aquarium for the animal, 26—inlet pipe, and 27—outlet pipe.
Figure 4:
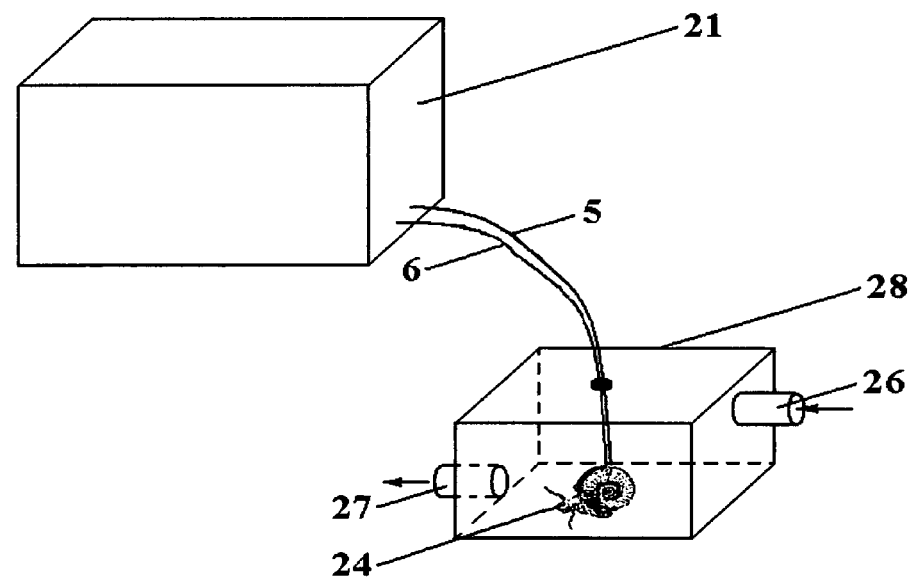
FIG. 4 shows a possible version of arranging the biological environment monitoring system in the case it is used to monitor the quality of air, for example, at waste-incinerating plants or at fuel-and-energy complex plants, where 28—chamber for the animal.

Electronic equipment in the biological environment monitoring system in the case it is used to monitor aquatic environment and bottom sediments of a water body (see FIG. 2) is placed in container 21 for equipment on a stage 20 whose platform is located above water level of the water body under investigation, while supports are mounted on land or in water area, on the bottom of water body under investigation. In this case, for example, crayfish, spiny crabs, crabs, oysters, mussels, ampularia and some unionide species are used as test animals 24. In the test animal's heart area on its hard outer covering 10, cylinder 2 of the installing element with two lobes 3 of the installing element are attached, for example, by gluing the latter to the test animal's outer covering 10. To accommodate test animal 24, a cage 22 for the animal is used, which can be made from metal or polymer net and have a slit 23 for optical fibres. Casing 1 together with transmitting optical fibre 5 and receiving optical fibre 6 is run through slit 23 for optical fibres, then casing 1 is inserted into cylinder 2 of the installing element and secured inside it with the help of fixing screw 4. Cage 22 for the animal with one test animal 24 inside is put down on the bottom of water body under investigation. If it is necessary to use several test animals 24 in the biological environment monitoring system, each of them is placed in a separate cage 22 for the animal, thus ensuring the absence of visual contact between test animals 24.

Where the biological environment monitoring system is used to monitor water quality at water treatment intake stations, a test animal 24 is placed (see FIG. 3) in running-water aquarium 25 for the animal, which can be made from glass and equipped with inlet pipe 26 and outlet pipe 27 connected to a water pump (not shown in the figures). In this case, for example, crayfish, some unionide species, as well as other benthos invertebrate species with a hard outer covering living in the water body under investigation are used as test animals 24.

Where the biological environment monitoring system is used to monitor air quality at waste-incinerating plants or fuel-and-energy complex plants, a test animal 24 (see FIG. 4) is placed in chamber 28 for the animal, which is made hermetic from glass and equipped with inlet pipe 26 and outlet pipe 27 connected to an air pump (not shown in the figures).

In this case, for examples, vine snails, achatines, scorpions or mole crickets are used as test animals 24.

The biological environment monitoring system being the subject of this invention and enabling to implement the biological environment monitoring method applied for operates as follows.

The operator of the biological environment monitoring system turns on power supply of electronic equipment incorporated in this system, including computer 19 and power supply 16 of the optical radiation source. Power supply 16 of the optical radiation source applies voltage to optical radiation source 14, which begins to emit optical radiation of near IR spectral range. This optical radiation, having passed through the input end of transmitting optical fibre 5, spreads along it to output end 7 and, on leaving output end 7 of transmitting optical fibre 5, falls on the test animal's outer covering 10 and through it penetrates into the body of test animal 24. Some part of optical radiation is reflected from the test animal's outer covering 10 and its internal organs, including from its heart.

Some part of optical radiation reflected by the test animal's outer covering 10 and its internal organs, including from its heart, comes to input end 8 of receiving optical fibre 6, spreads along it and, having passed through its output end, falls on sensitive surface of optical radiation receiver 15, which converts optical radiation to an electrical signal with an amplitude proportional to the incident light flow. During its work the heart of test animal 24 periodically changes its volume and shape (see the test animal's heart 11 during diastole period and the test animal's heart 12 during systole period in FIG. 1). As a result, the heart sac's boundaries shift relative to the optical radiation beam emerging from output end 7 of transmitting optical fibre 5 and change the value of light flow reflected by the heart and reaching input end 8 of receiving optical fibre 6 and irradiating optical radiation receiver 15. This is why, besides a constant component, an electrical signal formed by optical radiation receiver 15 also has a variable component whose period is equal to the heartbeat period of test animal 24. Said periodic variable component of the electrical signal has a rather complex a priori unknown shape that can be unstable in time due to movements of test animal 24.

The electrical signal formed by optical radiation receiver 15 and then amplified in power by amplifier 17 comes to analog-to-digital converter 18, which with the preset-time discreteness $\Delta t$ converts instantaneous values of electrical signal voltage to digital codes $x_i$ coming to computer 19. Computer 19 feeds every digital code $x_i$, which comes to it and corresponds to an instantaneous value of electrical signal voltage, to its memory together with the values of instants of current time $t_i$ when this digital code came.

After the entry of 2m digital codes $x_i$ corresponding to instantaneous values of electrical signal voltage at instants of time $t_i$, computer 19 starts performing digital filtration of digital codes matched to the shape and frequency of desired electrical signal. To this end, computer 19 determines estimates of the digital codes corresponding to instantaneous values of the electrical signal with zero constant component at instants of time $t_n=n\Delta t$ (n=m, m+1, m+2, ...) according to the expression $$\hat{x}_n = 1/(\pi \Delta t) \sum_{i=n-m+1}^{n+m} x_i(\sin(2\pi(f_0 + \Delta f)(t_i - t_n)) - \sin(2\pi(f_0 - \Delta f)(t_i - t_n)))/(t_i - t_n),$$

where $\Delta t$—interval of discreteness of electrical signal quantization in time when its instantaneous values are converted to digital codes; 2m—number of digital codes used during filtration; $f_0$—expected heartbeat frequency in the test invertebrate; $\Delta f$—the digital filter's pass half-band chosen, for example, in accordance with the expression $\Delta f=(0.1-0.8)f_0$.

Initial value of expected heartbeat frequency $f_0$ in the test invertebrate is sample and fed to computer 19 on the basis of data that was obtained during test registration of cardiac activity of a particular individual test animal 24 carried out before using this system for its proper purpose.

Computer 19 sends to its memory the obtained estimates $\hat{x}_n$ of digital codes together with the values of instants of current time $t_n=n\Delta t$ (n=m, m+1, m+2, ... ), for which these were calculated during digital filtration. In practice, the number 2m of digital codes used during filtration can amount to 9000-10000.

Then in accordance with known algorithms, e.g. by way of comparing with zero, computer 19 determines all pairs of estimates $\hat{x}_n$ of digital codes obtained for instants of current time $t_n=n\Delta t$ и $t_{n+1}=(n+1)\Delta t$ and whose signs change, e.g. from minus to plus as the values of instants of current time, for which these were obtained, grow. Further, computer 19 determines pairs of such estimates closest by the time of obtaining thereof and calculates values of the electrical signal period by way of computing the difference between the values of instants of current time, for which they were found, for example, sign-negative estimates of digital codes constituting two pairs of estimates closest by the time of obtaining. Computer 19 sends the set of computed values of electrical signal period to its memory, thus forming a preset-volume sample of values of the period of the electrical signal. In practice, volume K of this sample can make up 30 to 1000.

Then, during implementation of one version of the method applied for, computer 19 calculates a sample mean and sample dispersion of the formed sample of values of the electrical signal period according to the following expressions, respectively, $$M_T = 1/K \sum_{i=1}^{K} T_i \text{ and } D_T = 1/(K-1) \sum_{i=1}^{K} (T_i - M_T)^2,$$

where K—volume of the selection of values of the electrical signal period; $T_i$—sample value of the electrical signal period with number i.

In implementing another version of the method applied for, computer 19 calculates a sample mean and arithmetical mean of difference moduli for each two sample values, closest by the time of obtaining, of the electrical signal period of the formed sample of values of the electrical signal period according to the following expressions, respectively, $$M_T = 1/K \sum_{i=1}^{K} T_i \text{ and } E_r = 1/(K-1) \sum_{i=1}^{K-1} |T_{i+1} - T_i|,$$

where K—volume of the sample of values of the electrical signal period; $T_i$—sample value of the electrical signal period with number i.

Computer 19 also calculates the expected heartbeat frequency $f_0$ in the test animal as a value inverse to the sample mean_value of the electrical signal period, i.e. $f_0=1/M_T$ and later uses it to compute estimates of digital codes during digital filtration described above. Such adjustment of the expected test animal's heartbeat frequency $f_0$ in filtration algorithm is made by computer 19 with the preset periodicity during the entire time of functioning of the biological environment monitoring system.

In one version of implementing the method applied for, computer 19, in order to make a decision on the state of environment under investigation, can calculate the difference between reference value of sample dispersion of heartbeat period in test animal 24 stored in the memory of computer 19 and obtained at the stage of calibrating of the biological environment monitoring system during registration of the heartbeat signal from the same individual test animal 24 placed in high-quality environment, and the sample dispersion $D_T$ obtained for values of the electrical signal period, and then compares this difference with the threshold value set for it and stored in the memory of computer 19. If the difference obtained does not exceed the threshold value, computer 19 forms no ecological danger signal.

In another version of implementing the method applied for, computer 19, in order to make a decision on the state of environment under investigation, can calculate the difference between the reference value of arithmetical mean of difference moduli for each two, closest by the time of obtaining, sample values of heartbeat period in test animal 24 stored in the memory of computer 19 and obtained at the stage of calibrating the biological environment monitoring system during registration of the heartbeat signal from the same individual test animal 24 placed in high-quality environment, and arithmetical mean $E_T$ of difference moduli for each two, closest by the time of obtaining, sample values of the electrical signal period, and then compares this difference with the threshold value set for it and stored in the memory of computer 19. If the difference obtained does not exceed the threshold value, computer 19 forms no ecological danger signal.

In opinion of the authors of this invention, the best technical result is achieved when, in order to make a decision, the threshold value is compared with the product of sample mean by sample dispersion of the electrical signal period or the product of sample mean by square arithmetical mean of difference moduli for each two sample values of the electrical signal period closest by the time of obtaining.

In this case, to make a decision on the state of environment under investigation in one version of implementing this invention, computer 19 calculates the product $M_T D_T$ of sample mean by sample dispersion of the formed sample of values of the electrical signal period. Then computer 19 calculates the difference between the reference value of this product stored in the memory of computer 19 and determined at the stage of calibrating the biological environment monitoring system during registration of the heartbeat signal from the same individual test animal 24 placed in high-quality environment, and the obtained product of sample mean by sample dispersion of the formed sample of values of the electrical signal period. If the difference obtained does not exceed the threshold value set for it and stored in the memory of computer 19, then computer 19 also forms no ecological danger signal.

For making a decision on the state of environment under investigation in another version of implementing this invention, computer 19 calculates the product $M_T E_T^2$ of sample mean by square arithmetical mean of difference moduli for each two, closest by the time of obtaining, sample values of the formed sample of values of the electrical signal period. Then computer 19 calculates the difference between the reference value of this product stored in the memory of computer 19 and determined at the stage of calibrating the biological environment monitoring system during registration of the heartbeat signal from the same individual test animal 24 placed in high-quality environment, and the obtained product of sample mean by square arithmetical mean of difference moduli for each two, closest by the time of obtaining, sample values of the formed sample of values of the electrical signal period. If the difference obtained does not exceed the threshold value set for it and stored in the memory of computer 19, then computer 19 also forms no ecological danger signal.

In the case the level of contents of toxic substances suddenly grows, deterioration of the quality of environment under investigation leads to homeostasis derangement in the organism of conventionally healthy test animal 24 placed in it. This bring about a reaction of stress, at the initial stage of development of which, i.e. reaction of alarm, in healthy individuals a deviation of heartbeat period values from its sample mean value sharply and significantly decreases in comparison with quiet state in which a fairly wide spread thereof is observed. Therefore, both the sample dispersion $D_T$ of the selection of values of the electrical signal period and arithmetic mean $E_T$ of difference moduli for each two, closest by the time of obtaining, sample values of the formed sample of values electrical signal period considerably reduces as well.

In this case, when implementing one version of the method applied for, the difference calculated by computer 19 between the stored reference value of sample dispersion of heartbeat period obtained at quiet state of test animal 24 and the obtained sample dispersion $D_T$ of the sample of values of the electrical signal period, when test animal 24 was subjected to stress, exceeds while comparing it the threshold value set for it and stored in the memory of computer 19. Then computer 19 forms an ecological danger signal.

When implementing in this situation another version of the method applied for, the difference calculated by computer 19 between the stored reference value of arithmetical mean of difference moduli for each two, closest by the time of obtaining, sample values of the formed sample of values of the heartbeat period obtained at quiet state of test animal 24, and the obtained arithmetical mean $E_T$ of difference moduli for each two, closest by the time of obtaining, sample values of the formed sample of values of the electrical signal period, when test animal 24 was subjected to stress, exceeds, while comparing it, the threshold value stored in the memory of computer 19. In this case, computer 19 forms an ecological danger signal.

As was noted above, the reaction of alarm in test animal 24 at the initial stage of development of stress in majority of species and their individuals is accompanied not only by a sharply and significantly decreased deviation of the heartbeat period from its sample mean value, but also by a reduction of the very heartbeat period in test animal 24.

Therefore, for one version of implementing the method applied for in the case of stress in test animal 24 due to deterioration of environment quality the difference between reference value of the product of sample mean by sample dispersion and the obtained product $M_T D_T$ of sample mean by sample dispersion of the formed sample of values of the electrical signal period when compared by computer 19, exceeds the threshold value set for it, which results in that computer 19 also forms an ecological danger signal.

For another version of implementing the method applied for in the case of stress in test animal 24 due to deterioration of environment quality the difference between reference value of the product of sample mean by square arithmetical mean of difference moduli for each two, closest by the time of obtaining, sample values of the formed sample of heartbeat period values and the obtained product $M_T E_T^2$ of sample mean by square arithmetical mean of difference moduli for each two, closest by the time of obtaining, sample values of the formed sample of values of the electrical signal period, exceeds while being compared by computer 19 the threshold value set for it, which results in that computer 19 also forms an ecological danger signal.

Information on the rise of ecological danger is displayed for the operator of the biological environment monitoring system on the monitor of computer 19. Moreover, an ecological danger warning can be given by a sonic and light signaling device connected to computer 19 (not shown in the figures).

In the case the biological environment monitoring system forms an ecological danger signal, water, air, soil or bottom sediments under investigation are sampled for their subsequent chemical analysis, by the results of which a final decision is made about the state of environment.

INDUSTRIAL APPLICABILITY

The authors of this invention worked out experimental models of the biological environment monitoring system being the subject of this invention and realizing the method applied for. In August-October of 2005 these experimental models of the system were tested in laboratory and full-scale conditions on water bodies in Saint-Petersburg and Leningrad province (Russia) for the purposes of monitoring the quality of aquatic environment, using crayfish and mollusks living in water as test animals, as well as in laboratory conditions for the purposes of monitoring the quality of air environment, using vine snails and achatines as test animals. The tests showed a rather high efficiency of using the biological environment monitoring system for increasing reliability of monitoring the quality of environment components.

Thus, the biological environment monitoring method (versions) and the system for its implementation ensure higher reliability of environment monitoring, widening of functionalities, as well as lower cost and simpler operation of the biological environment monitoring system.

The invention claimed is:

1. A method of biological environment monitoring including:
   placing a test invertebrate with a hard outer covering in the environment under investigation;
   exposing the test invertebrate's heart area to optical radiation of IR spectral range;
   receiving and converting the optical radiation reflected by the test invertebrate's heart to an electrical signal;
   amplifying the electrical signal obtained;
   converting its instantaneous values to digital codes;
   entering the digital codes obtained to a computer;
   determining and memorizing with the help of the computer a preset-volume sample of values of the period of the electrical signal;
   determining with the help of the computer a statistical characteristic of the sample of values of the electrical signal period;
   comparing with the help of the computer the obtained statistical characteristic with the threshold value set for it; and
   forming an ecological danger signal on the basis of comparison results, differing in that
   the test invertebrate is exposed to optical radiation of IR spectral range with the help of a transmitting optical fibre with its output end placed on the test invertebrate's hard outer covering within its heart area and an optical radiation source mounted so that it can have optical contact with the input end of the transmitting optical fibre;
   the optical radiation reflected by the test invertebrate's heart is received by a receiving optical fibre with its input end located on the test invertebrate's hard outer covering within its heart area;
   the optical radiation reflected by the test invertebrate's heart is converted to an electrical signal with the help of the optical radiation receiver mounted so that can have optical contact with the output end of the receiving optical fibre;
   before determining a sample of values of the period of electrical signal, digital filtration of digital codes which is matched to the shape and frequency of the electrical signal is made by the computer;
   a sample dispersion is determined as a statistical characteristic for the sample of values of the electrical signal period, and
   an ecological danger signal is formed, should the threshold value exceed the obtained sample dispersion of values of the electrical signal period.

2. A method according to claim 1, wherein the test invertebrate is exposed to optical radiation and the optical radiation reflected by the test invertebrate's heart is received with the help of the transmitting and receiving optical fibres with, respectively, their output end and input end facing one side and positioned relative to each other at a distance satisfying the inequality $$(\pi d^2 P)^{0.07} - 2.2(1/(\pi d^2 P))^{0.02} \leq R \leq (\pi d^2 P)^{0.07} + 2.2(1/(\pi d^2 P))^{0.02},$$

where R—distance between the output end of the transmitting optical fibre and input end of the receiving optical fibre, mm; P—output power of the optical radiation source, mW; d—diameter of the transmitting optical fibre or receiving optical fibre, μm.

3. A method according to claim 1, wherein during digital filtration of digital codes the estimates of digital codes are determined which correspond to instantaneous values of an electrical signal with zero constant component at the instants of time $t_n = n\Delta t$ (n=m, m+1, m+2, . . . ), according to the expression $$\hat{x}_n = 1/(\pi \Delta t) \sum_{i=n-m+1}^{n+m} x_i (\sin(2\pi(f_0 + \Delta f)(t_i - t_n)) - \sin(2\pi(f_0 - \Delta f)(t_i - t_n)))/(t_i - t_n),$$

where Δt—interval of discreteness of electrical signal quantization in time when its instantaneous values are converted to digital codes; 2m—number of digital codes used during filtration; $f_0$—expected heartbeat frequency in the test invertebrate; Δf—digital filter's pass half-band, Δf=(0.1-0.8)$f_0$.

4. A method according to claim 1, wherein a sample mean value is determined as a statistical characteristic of the sample of values of the electrical signal period.

5. A method according to claim 1 or 4, wherein an ecological danger signal is formed if the threshold value exceeds the product of sample mean by sample dispersion of values of the electrical signal period.

6. A method according to claim 1, 3 or 4, wherein the expected heartbeat frequency $f_0$ in the test invertebrate is determined as a value inverse to the sample mean value of the electrical signal period.

7. A method according to claim 1, wherein the volume of the selection of values of the electrical signal period is set within the limits of 30 to 1000.

8. A method of biological environment monitoring including:
   placing the test invertebrate with a hard outer covering in the environment under investigation;
   exposing the test invertebrate's heart area to optical radiation of IR spectral range;
   receiving and converting the optical radiation reflected by the test invertebrate's heart to an electrical signal;
   amplifying the electrical signal obtained;
   converting its instantaneous values to digital codes;
   entering the obtained digital codes to a computer;
   determining and memorizing with the help of the computer the preset-volume sample of values of the period of the electrical signal;
   determining with the help of the computer a statistical characteristic of the sample of values of the electrical signal period;
   comparing with the help of the computer the obtained statistical characteristic with the threshold value set for it; and
   forming an ecological danger signal on the basis of comparison results, differing in that
   the test invertebrate is exposed to optical radiation of IR spectral range with the help of the transmitting optical fibre with its output end placed on the test invertebrate's hard outer covering within its heart area and the optical radiation source mounted so that it can have optical contact with the input end of the transmitting optical fibre;
   the optical radiation reflected by the test invertebrate's heart is received with the help of the receiving optical radiation fibre with its input end placed on the test invertebrate's hard outer covering within its heart area;
   the optical radiation reflected by the test invertebrate's heart is converted to an electrical signal with the help of the optical radiation receiver mounted so that it can have optical contact with the output end of the receiving optical fibre;
   before determining the sample of values of the electrical signal period, digital filtration of digital codes which is matched to the electrical signal's shape and frequency is made by the computer;
   the arithmetical mean of difference moduli for each two sample values of the electrical signal period closest by the time of obtaining is determined as a statistical characteristic of the sample of values of the electrical signal period; and
   an ecological danger signal is formed in case the threshold value exceeds the obtained arithmetical mean of difference moduli for each two sample values of the electrical signal period closest by the time of obtaining.

9. A method according to claim 8, wherein the test invertebrate is exposed to optical radiation and the optical radiation reflected by the test invertebrate's heart is received with the help of the transmitting and receiving optical fibres with, respectively, their output end and input end facing one side and positioned relative to each other at a distance satisfying the inequality $$(\pi d^2 P)^{0.07} - 2.2(1/(\pi d^2 P))^{0.02} \leq R \leq (\pi d^2 P)^{0.07} + 2.2(1/(\pi d^2 P))^{0.02},$$

where R—distance between the output end of the transmitting optical fibre and input end of the receiving optical fibre, mm; P—output power of the optical radiation source, mW; d—diameter of the transmitting optical fibre or receiving optical fibre, μm.

10. A method according to claim 8, wherein during digital filtration of digital codes the estimates of digital codes are determined which correspond to instantaneous values of the electrical signal with zero constant component at the instants of time $t_n = n\Delta t$ (n=m, m+1, m+2, ... ), according to the expression $$\hat{x}_n = 1/(\pi \Delta t) \sum_{i=n-m+1}^{n+m} x_i (\sin(2\pi(f_0 + \Delta f)(t_i - t_n)) - \sin(2\pi(f_0 - \Delta f)(t_i - t_n)))/(t_i - t_n),$$

where Δt—interval of discreteness of electrical signal quantization in time when its instantaneous values are converted to digital codes; 2m—number of digital codes used during filtration; $f_0$—expected heartbeat frequency in the test invertebrate; Δf—digital filter's pass half-band, Δf=(0.1-0.8)$f_0$.

11. A method according to claim 8, wherein a sample mean value is determined as a statistical characteristic of the sample of values of the electrical signal period.

12. A method according to claim 8 or 11, wherein an ecological danger signal is formed if the threshold value exceeds the product of sample mean by square arithmetical mean of difference moduli for each two sample values of the electrical signal period closest by the time of obtaining.

13. A method according to claim 8, 10 or 11, wherein the expected heartbeat frequency $f_0$ in the test invertebrate is determined as a value inverse to the sample mean value of the electrical signal period.

14. A method according to claim 8, wherein the volume of the sample of values of the electrical signal period is set within the limits of 30 to 1000.

15. A system for biological environment monitoring comprising a computer and at least one shaper of a digital signal of cardiac activity in the form of series-connected cardiac activity sensor including a casing with an element for installing on the body of the test invertebrate with a hard outer covering, an optical radiation source and optical radiation receiver; amplifier whose input is connected to the optical radiation receiver output; and an analog-to-digital converter whose output is connected to the computer input, differing in that its cardiac activity sensor is equipped with a transmitting optical fibre and receiving optical fibre, the input end of the transmitting optical fibre and output end of the receiving optical fibre being located so that they can have optical contact, respectively, with the optical radiation source and optical radiation receiver, while the output end of the transmitting optical fibre and input end of the receiving optical fibre face one side and are positioned within the casing at a distance satisfying the inequality $$(\pi d^2 P)^{0.07} - 2.2(1/(\pi d^2 P))^{0.02} \leq R \leq (\pi d^2 P)^{0.07} + 2.2(1/(\pi d^2 P))^{0.02},$$

where R—distance between the output end of the transmitting optical fibre and input end of the receiving optical fibre, mm; P—output power of the optical radiation source, mW; d—diameter of the transmitting optical fibre or receiving optical fibre, µm.

16. A system according to claim 15, wherein a semiconductor laser made with the possibility of emitting optical radiation of IR spectral range is used as an optical radiation source for the cardiac activity sensor.

17. A system according to claim 15, wherein a light-emitting diode made with the possibility to emit optical radiation of IR spectral range is used as an optical radiation source for the cardiac activity sensor.

\* \* \* \* \*